(12) United States Patent  (10) Patent No.: US 8,497,227 B2
Saito et al. (45) Date of Patent: Jul. 30, 2013

(54) DIPHENYLSULFONE BRIDGED COMPOUND, COLOR FORMING SUBSTANCE FOR THERMAL RECORDING AND THERMAL RECORDING MATERIAL

(75) Inventors: Hajime Saito, Sabae (JP); Takeo Hasegawa, Sakai (JP)

(73) Assignee: Nicca Chemical Co., Ltd., Fukui-shi (JP)

( * ) Notice: Subject to any disclaimer, the term of this patent is extended or adjusted under 35 U.S.C. 154(b) by 282 days.

(21) Appl. No.: 13/055,904

(22) PCT Filed: Jul. 28, 2008

(86) PCT No.: PCT/JP2008/063923
§ 371 (c)(1),
(2), (4) Date: Jan. 25, 2011

(87) PCT Pub. No.: WO2010/013352
PCT Pub. Date: Feb. 4, 2010

(65) Prior Publication Data
US 2011/0136664 A1 Jun. 9, 2011

(51) Int. Cl.
*B41M 5/333* (2006.01)
(52) U.S. Cl.
USPC .............. 503/216; 503/225; 568/31; 568/32; 568/33; 568/34

(58) Field of Classification Search
None
See application file for complete search history.

(56) References Cited

U.S. PATENT DOCUMENTS

| 3,539,375 | A | 11/1970 | Baum et al. |
| 5,420,094 | A | 5/1995 | Araki et al. |
| 6,037,308 | A | 3/2000 | Sato et al. |
| 2003/0186810 | A1 | 10/2003 | Kato |

FOREIGN PATENT DOCUMENTS

| DE | 10012850 A1 | 9/2000 |
| EP | 0 860 429 A1 | 8/1998 |
| EP | 2 181 854 A1 | 5/2010 |
| JP | 43-4160 | 6/1968 |
| JP | 05-301446 A | 11/1993 |
| JP | 07-149713 A | 6/1995 |
| JP | 10-29969 A | 2/1998 |
| JP | 2000-135868 A | 5/2000 |
| JP | 2001-232949 A | 8/2001 |
| JP | 2006-149446 A | 6/2006 |
| JP | 2006-297783 A | 11/2006 |
| JP | 2008-8280283 A | 11/2008 |

OTHER PUBLICATIONS

Supplementary European Search Report mailed on Nov. 16, 2012 for EP 08792131.8.
Supplementary European Search Report mailed on Nov. 5, 2012 for EP 08792131.8.
Wawrzyniec Podkoscielny et al, Angewadte Makromolekulare Chemie, 1991, pp. 143-153, vol. 188.

*Primary Examiner* — Bruce H Hess
(74) *Attorney, Agent, or Firm* — Holtz Holtz Goodman & Chick PC

(57) ABSTRACT

Diphenylsulfone bridged compounds of the general formula: (1) wherein n is an integer of 1 to 10. Further, there is disclosed a thermal recording material comprising a support and, superimposed thereon, a thermosensitive color forming layer containing a color forming substance for thermal recording consisting of any of the diphenylsulfone bridged compounds and a color forming substance consisting of a colorless or light-colored leuco dye. This thermal recording material excels in the storability, especially wet heat resistance and oil resistance, of image areas and further exhibits excellent characteristics in the storability, especially heat resistance, of undeveloped areas.

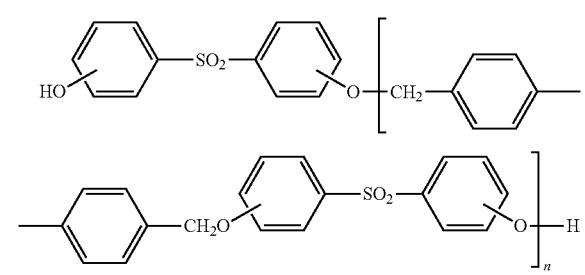

(1)

3 Claims, No Drawings

DIPHENYLSULFONE BRIDGED COMPOUND, COLOR FORMING SUBSTANCE FOR THERMAL RECORDING AND THERMAL RECORDING MATERIAL

This application is the United States national phase application of International Application PCT/JP2008/063923 filed Jul. 28, 2008.

TECHNICAL FIELD

The present invention relates to a diphenylsulfone bridged compound, a color forming substance for thermal recording and a thermal recording material. More particularly, the present invention relates to a novel diphenylsulfone bridged compound useful as a color forming substance which can provide a thermal recording material exhibiting excellent storage property of image portions and excellent storage property of undeveloped portions, a color forming substance for thermal recording comprising the bridged compound and a thermal recording material exhibiting the above excellent properties.

BACKGROUND ART

A thermal recording material is, in general, a material comprising a heat-sensitive color forming layer which comprises a colorless or light-colored electron-donating dye precursor and an electron-accepting color forming substance as the main components and is disposed on a support. The dye precursor and the color forming substance instantaneously react with each other by heating with a heated head, a heated pen or a laser beam, and a recorded material can be obtained. The thermal recording material described above has been developed for a long time. For example, as the heat-sensitive sheet for copying obtained by coating a paper with a specific coating layer comprising a composition which is colorless under the normal condition and develops color by heating or irradiation with infrared light, a heat-sensitive sheet for copying comprising a colorless dye base of the lactone, lactam or sultone type, an organic acid and a substance melting under heating as the reactive color forming component, is proposed (Patent Reference 1). As the thermal recording material which exhibits improved moisture resistance and stability during printing and can prevent coloring during drying and preparation of a coating component for forming records due to the improved moisture resistance, a thermal recording material in which the unit for forming records comprises a support sheet material comprising crystal violet lactone and a phenolic substance, the phenolic substance is a solid substance at the room temperature and liquefied or vaporized at the temperature of a thermograph to form records by the reaction with the lactone, and the lactone and the phenolic substance are dispersed in polyvinyl alcohol, is proposed (Patent Reference 2).

The thermal recording materials described above have advantages in that records can be obtained by relatively simple apparatuses, maintenance is facilitated, and generation of noise is suppressed and are utilized for thermal printers of various portable terminals, medical image printers attached to ultrasonic echo instruments and the like, thermopen recorders of cardiographs and analytical instruments, air plane tickets, train tickets and PUS labels for merchandises.

Various properties such as excellent color forming property, color formation in a great density with small amount of heat, excellent storage properties of the obtained images and maintenance of whiteness in undeveloped portions, are required for a thermal recording material. In particular, excellent storage properties such as excellent oil resistance, moisture resistance and heat resistance are required for labels for food processed by microwave ovens, parking tickets, delivery labels and tickets since reliability of recorded images is important Therefore, various compounds have been examined as the developer in thermal recording materials.

For example, thermal recording materials comprising α,α'-bis[4-(p-hydroxyphenylsulfonyl)phenoxy]-p-xylene, α,α'-bis[4-(p-hydroxyphenylsulfonyl)phenoxy]-m-xylene or α,α'-bis[4-(p-hydroxy-phenylsulfonyl)phenoxy]-o-xylene are proposed as the color developer providing a thermal recording material which exhibits great sensitivity, suppresses fog in the background and exhibits excellent storage properties, in particular, excellent resistance to water and plasticizers (Patent Reference 3). As the color developer for thermal recording materials exhibiting excellent storage stability of images obtained by the color formation, in particular, excellent resistance to plasticizers, oils, light and moisture under heat, diphenylsulfone bridged compounds as the reaction products of dihydroxydiphenylsulfone and alkylene dichlorides or α,α'-dichloroxylene are shown as examples (Patent Reference 4). However, the heat resistance of undeveloped portions is insufficient in the thermal recording materials described above, and the requirement for the excellent storage properties of developer is not sufficiently satisfied,

[Patent Reference 1] Japanese Patent Application Publication Showa 43(1968)-4160

[Patent Reference 2] Japanese Patent Application Publication Showa 45(1970)-14039

[Patent Reference 3] Japanese Patent Application Laid-Open No. Heisei 7(1995)-149713

[Patent Reference 4] Japanese Patent Application Laid-Open No. Heisei 10(1998)-29969

DISCLOSURE OF THE INVENTION

Problems to be Overcome by the Invention

Under the above circumstance, the present invention has an object of providing a novel diphenylsulfone derivative useful as the color forming substance which can provide a thermal recording material exhibiting excellent storage properties, in particular, excellent oil resistance and resistance to moisture under heat, of image portions and excellent storage properties, in particular, heat resistance, of undeveloped portions, a color forming substance for thermal recording comprising the diphenylsulfone derivative and a thermal recording material using the color forming substance and exhibiting the above excellent properties.

Means for Overcoming the Problems

As the result of intensive studies by the present inventors to achieve the above object, it was found that the object could be achieved with a diphenylsulfone bridged compound having a specific structure. The present invention has been completed based on the knowledge.

The present invention provides:
[1] A diphenylsulfone bridged compound represented by general formula (1):

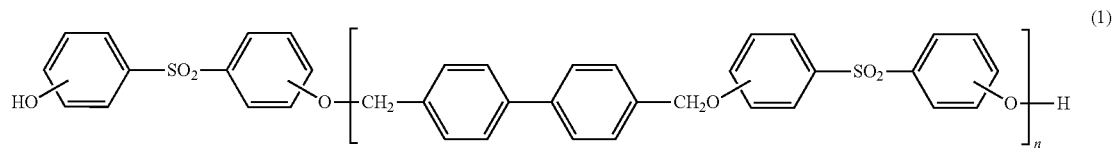

wherein n represents an integer of 1 to 10;
[2] A color forming substance for thermal recording comprising a diphenylsulfone bridged compound represented by general formula (1):

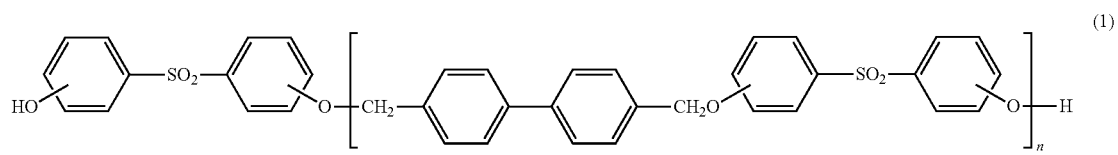

wherein n represents an integer of 1 to 10; and
[3] A thermal recording material comprising a heat-sensitive color forming layer which comprises a color forming substance for thermal recording comprising a diphenylsulfone bridged compound represented by general formula (1);

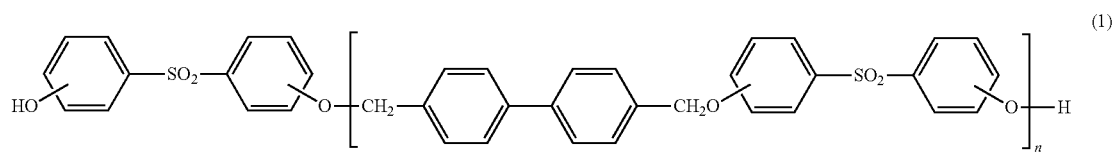

wherein n represents an integer of 1 to 10, and a color forming substance comprising a colorless or light-colored leuco dye, and is disposed on a support.

THE EFFECT OF THE INVENTION

In accordance with the present invention, the novel diphenylsulfone bridged compound useful as the color forming substance which can provide a thermal recording material exhibiting excellent storage properties, in particular, excellent oil resistance and resistance to moisture under heat, of image portions and excellent storage properties, in particular, heat resistance, of undeveloped portions, the color forming substance for thermal recording comprising the diphenylsulfone bridged compound and the thermal recording material using the color forming substance and exhibiting the above excellent properties, can be provided.

THE MOST PREFERRED EMBODIMENT TO CARRY OUT THE INVENTION

The diphenylsulfone bridged compound of the present invention will be described in the following.
[Diphenylsulfone Bridged Compound]
The diphenylsulfone bridged compound of the present invention is a novel compound and has a structure represented by general formula (1):

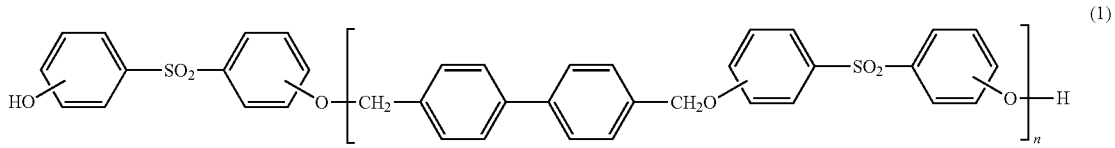

(1)

wherein n represents an integer of 1 to 10.

The diphenylsulfone bridged compound described above is useful, in particular, as the color forming substance in thermal recording materials.

The process for producing the diphenylsulfone bridged compound represented by general formula (1) is not particularly limited and can be produced, for example, by dehydrohalogenation from a dihydroxydiphenylsulfone and a 4,4'-bis(halomethyl)biphenyl (chloromethyl or bromomethyl being preferable as the halomethyl) in the presence of a basic substance using a solvent. It is preferable that the temperature of the reaction is 50° C. or higher and the refluxing temperature of the solvent or lower. When the temperature of the reaction is lower than 50° C. there is the possibility that a long time is required before the reaction is completed. When the temperature of the reaction exceeds the refluxing temperature of the solvent, a pressure resistant reactor is necessary, and there is the possibility that economy of the process is adversely affected.

Examples of the dihydroxydiphenylsulfone used for the reaction include 4,4'-dihydroxydiphenylsulfone, 2,4'-dihydroxydiphenylsulfone, 2,2'-dihydroxydiphenylsulfone and mixtures of these compounds. Among these compounds, mixtures of 4,4'-dihydroxydiphenylsulfone and 2,4'-dihydroxydiphenylsulfone are preferable since a color forming substance exhibiting excellent storage properties, in particular, excellent oil resistance and resistance to moisture under heat, of image portions and excellent heat resistance of undeveloped portions can be obtained.

Examples of the basic substance used in the above include sodium hydroxide, potassium hydroxide, sodium carbonate, potassium carbonate, tirethylamine and pyridine.

Examples of the solvent used in the above include alcohols such as methanol, ethanol, propanol, isopropanol, butanol and isobutanol; glycols such as ethylene glycol, propylene glycol, diethylene glycol and dipropylene glycol; monoalkyl ethers of the glycols; dialkyl ethers of the glycols; ketones such as acetone and methyl ethyl ketone; nitriles such as acetonitril and propionitrile; ethers such as tetrahydrofuran; esters such as methyl acetate, dimethyl carbonate and propylene carbonate; amides such as N-methylformamide and N,N-dimethylformamide; sulfoxides such as dimethyl sulfoxide; and mixed solvents of these solvents.

In the present invention, n represents an integer of 1 to 10 in general formula (1). When n represents an integer exceeding 10, the concentration of the terminal hydroxyl group present in the bridged compound represented by general formula (1) is decreased, and there is the possibility that the effect as the color forming substance is decreased.

In the production of the diphenylsulfone bridged compound represented by general formula (1), it is preferable that the ratio of the amount by mole of the dihydroxydiphenylsulfone to the amount by mole of the bis(halomethyl)biphenyl is 10:3 to 10:10 and more preferably 10:5 to 10:8. When the amount of the bis(halomethyl)biphenyl is less than 3 mole per 10 mole of the dihydroxydiphenylsulfone, the increase in the degree of condensation of the obtained bridged compound is suppressed, and there is the possibility that the amount of the unreacted dihydroxydiphenylsulfone in the reaction mixture is increased. When the amount of the bis(halomethyl)biphenyl exceeds 10 mole per 10 mole of the dihydroxydiphenylsulfone, there is the possibility that the concentration of the terminal hydroxyl group in the reaction product is decreased.

When the condensation reaction of the dihydroxydiphenylsulfone and the 4,4'-bis(halomethyl)biphenyl is conducted while the dihydroxy-diphenylsulfone is present in an excessive amount, the unreacted dihydroxydiphenylsulfone is occasionally mixed into the reaction mixture. The dihydroxydiphenylsulfone mixed into the reaction mixture can be separated and removed from the diphenylsulfone bridged compound by purification. Alternatively, the diphenylsulfone bridged compound containing the unreacted dihydroxydiphenylsulfone may be used without removing the dihydroxydiphenylsulfone as the color forming substance for thermal recording since the dihydroxydiphenylsulfone itself exhibits the property as the color forming substance. However, there is the possibility that the storage properties of the thermal recording material are decreased when the content of the dihydroxydiphenylsulfone is great.

The present invention also provides a color forming substance for thermal recording materials comprising the diphenylsulfone bridged compound represented by general formula (1).

The thermal recording material of the present invention is described in the following.

[Thermal Recording Material]

The thermal recording material of the present invention is characterized in that the thermal recording material comprises a heat-sensitive color forming layer which comprises the color forming substance for thermal recording comprising the diphenylsulfone bridged compound represented by general formula (1) and a color forming substance comprising a colorless or light-colored leuco dye and is disposed on a support.

(Color Forming Substance)

In the present invention, the colorless or light-colored leuco dye used as the color forming substance is not particularly limited. Examples of the colorless or light-colored leuco dye include fluorane derivatives, quinazoline derivatives, phthalide derivatives, triphenylmethane derivatives derivatives and phenothiazine derivatives. Among these leuco dyes, fluorane derivatives are preferable due to the excellent color forming property. Examples of the leuco dye of the fluorane derivative include 3-diethylamino-6-methyl-7-anilinofluorane, 3-diethylamino-6-methyl-7-(2',4'-dimethylanilino)fluorane, 3-diethylamino-6-methyl-7-chlorofluorane, 3-dibuthylamino-6-methyl-7-anilinofluorane, 3-diamylamino-6-methyl-7-anilinofluorane, 3-(N-methyl-N-propyl)amino-6-methyl-7-anilinofluorane, 3-(N-methyl-N-butyl)amino-6-methyl-7-anilinofluorane, 3-(N-methyl-N-amyl)amino-6-methyl-7-anilinofluorane, 3-(N-methyl-N-cyclohexyl)-amino-6-methyl-7-anilinofluorane, 3-(N-ethyl-N-propypl)amino-6-methyl-7-anilinofluorane, 3-(N-ethyl-N-amyl)amino-6-methyl-7-anilinofluorane, 3-(N-ethyl-N-isoamyl)amino-6-methyl-7-anilinofluorane, 3(N-ethyl-N-(4-methylphenyl)]amino-6-methyl-7-anilinofluorane, 3-(N- ethyl-N-cyclohexyl)amino-6-methyl-7-anilinofluorane, 3-(N-pentyl-N-cyclohexyl)-amino-6-methyl-7-anilinofluorane, 3-(N-hexyl-N-isoamyl)amino-6-methyl-7-anilinofluorane, 3-diethyl-N-butylamino-7-(2'-fluoroanilino)fluorane, 3-(N-methyl-N-cyclohexyl)amino-6-chlorofluorane, 3-pyrrolidyl-7-dibenzylaminofluorane, 3-bis(diphenylamino) fluorane, 3-diethylamino-6-chloro-7-anilinofluorane, 3-diethylamino-7-(2'-chloroanilino)fluorane, 3-dibutylamino-7-(2'-chloroanilino)fluorane, 3-diethylamino-7-chlorofluorane, 3-butylamino-7-(2'-chloroanilino)fluorane, 3-diethylamino-6-ethoxyethyl-7-anilinofluorane and 3-diethylamino-7-dibenzylaminofluorane. The amount of the color forming substance in the heat-sensitive color forming layer can be suitably selected in accordance with the properties of the thermal recording material to be prepared.

(Color Forming Substance)

In the present invention, as the color forming substance, the diphenylsulfone bridged compound represented by general formula (1) may be used singly or in combination with conventional color forming substances. By using the diphenylsulfone crosslinking compound represented by general formula (1) used in the present invention in combination with conventional color forming substances, further improvement in the storage properties of image portions and undeveloped portions is made possible without adversely affecting the color forming property of the conventional color forming substances.

The conventional color forming substance which can be used is not particularly limited. Examples of the conventional color forming substance include α-naphthol, β-naphthol, 4-octylphenol, p-t-octylphenol, p-t-butylphenol, p-phenylphenol, 1,1-bis(4-hydroxyphenyl)propane, 2,2-bis(4-hydroxyphenyl)propane, 2,2-bis(3-methyl-4-hydroxyphenyl)-propane, 2,2-bis(3-phenyl-4-hydroxyphenyl)propane, 2,2-bis(3,4-di-hydroxyphenyl)propane, 2,2-bis(2-chloro-4-hydroxyphenyl)propane, 2,2-bis(2,5-dibromo-4-hydroxyphenyl)propane, 2,2-bis(2-hydroxyphenyl)-propane, 2,2-bis(3-t-butyl-4-hydroxyphenyl)propane, 2,2-bis(p-hydroxy-phenyl)butane, 1,1,3-tris(2-methyl-4-hydroxy-5-t-butylphenyl)butane, 1,1,3-tris(2-methyl-4-hydroxy-5-cyclohexylphenyl)butane, 1,6-bis(4-hydroxybenzoyloxymethyl)hexane, 1,1-bis(4-hydroxyphenyl)cyclohexane, 1,1-bis(4-hydroxyphenyl)-1-phenylethane, bis(2-hydroxy-4-chlorophenyl)-methane, bis(4-hydroxyphenyl)methane, 1,3-bis(4-hydroxycumyl) benzene, 1,4-bis(4-hydroxycumyl)benzene, 1,4-bis(4'-hydroxybenzoyloxymethyl)-benzene, 1,4-bis(4-hydroxybenzoyloxymethyl)cyclohexane, 1,3-bis(3'-hydroxybenzoyloxymethyl)cyclohexane, 1,2-bis(2'-hydroxylbenzoyloxy-methyl)cyclohexane, α,α-bis(4-hydroxyphenyl)-α-methyltoluene, 4,4'-thio-bisphenol, 4,4'-thiobis(2-methylphenol), 4,4'-thiobis(2-chlorophenol), 4,4'-thiobis(6-tertiary-butyl-2-methylphenol), 1,7-bis(4-hydroxyphenyl-thio)-3,5-dioxaheptane, 1,5-bis(4-hydroxyphenylthio)-3-oxapentane, 1,3-bis((4-hydroxyphenylthio)propane, 1,3-bis(4-hydroxyphenylthio)-2-hydroxypropane, 4,4'-diphenol sulfoxide, 4,4'-dihydroxydiphenylsulfone, 2,4'-dihydroxydiphenylsulfone, 3,3'-diallyl-4,4'-diphenolsulfone, 4-allyloxy-4'-hydroxydiphenylsulfone, 4-benzyloxy-4'-hydroxydiphenylsulfone, 4-isopropoxy-4'-hydroxydiphenylsulfone, 4-propoxy-4'-hydroxydiphenyl-sulfone, 4-methyl-4'-hydroxydiphenylsulfone, 4-methyl-3',4'-dihydroxy-diphenylsulfone, 4,4'-dihydroxydiphenylsulfone diethyl ether condensates, methyl bis (4-hydroxyphenyl)acetate, butyl bis(4-hydroxyphenyl) acetate, benzyl bis(4-hydroxyphenyl)acetate, benzyl p-hydroxybenzoate, ethyl p-hydroxybenzoate, isopropyl p-hydroxybenzoate, dibenzyl 4-hydroxy-phthalate, dimethyl 4-hydroxyphthalate, ethyl 5-hydroxyisophthalate, 3,5-di-t-butylsalycilic acid, stearyl gallate, lauryl gallate, octyl gallate, N,N'-diphenylthiourea, N,N'-di(m-chlorophenyl)thiourea, N-(p-toluene-sulfonyl)-N'-(3-p-toluenesulfonyloxyphenyl)urea, N-(p-toluenesulfonyl)-N'-(p-butoxyphenyl)urea, N-(p-toluenesulfonyl)-N'-phenylurea, 2-hydroxy-3-naphthoic acid, 2-hydroxy-1-naphthoic acid and 1-hydroxy-2-naphthoic acid.

The color forming substance may be used singly or in combination of two or more.

(Sensitizer)

The thermal recording material of the present invention may further comprise sensitizers in the heat-sensitive color forming layer. The sensitizer used in the above is not particularly limited. Examples of the sensitizer include amides of fatty acid such as stearamide and palmitamide, 1,2-diphenoxyethane, 1,2-bis(4-methylphenoxy)-ethane, 1,2-bis(3-methylphenoxy)ethane, 1,2-bis(phenoxymethyl)benzene, 1,3-bis(phenoxymethyl)benzene, 1,4-bis(phenoxymethyl) benzene, 1,2-bis-(3-methylphenoxymethyl)benzene, 1,3-bis (3-methylphenoxymethyl)-benzene, 1,4-bis(3-methylphenoxymethl)benzene, 1,2-bis(4-methylphenoxymethyl) benzene, 1,3-bis(4-methylphenoxymethyl)benzene, 1,4-bis-(4-methylphenoxymethyl)benzene, 2-benzyloxynaphthalene, dibenzyl oxalate, di(4-methylbenzyl) oxalate, di(4-chlorobenzyl) oxalate, 4-acetyl-benzyl, N-phenyltoluenesulfonamide, naphthyl toluenesulfonate, p-benzylbiphenyl, m-terphenyl, 4,4'-dipropoxydiphenylsulfone, 4,4'-diisopropoxydiphenylsulfone, 4,4'-diallyloxydiphenylsulfone, 2,4'-dipropxydiphenylsulfone, 2,4'-diisopropoxydiphenylsulfone, 2,4'-diallyloxydiphenylsulfone, benzyl p-benzyloxybenzoate and benzyl terephthalate. The sensitizer may be used singly or in combination of two or more.

(Image Stabilizer)

The thermal recording material of the present invention may further comprise image stabilizers in the heat-sensitive color forming layer. The image stabilizer used in the above is not particularly limited. Examples of the image stabilizer include 4-benzyloxy-4'-(2-methylglycidyloxy)diphenylsulfone, 4,4'-diglycidyloxydiphenylsulfone, 4,4'-butylidenebis (3-methyl-6-t-butylphenol), 2,2'-di-t-butyl-5,5'-dimethyl-4,4'-sulfonylphenol, 1,1,3-tris(2-methyl-4-hydroxy-5-t-butylphenyl)butane, 1,1,3-tris(2-methyl-4-hydroxy-5-cyclohexylphenyl)butane, compounds having a polyester structure such as polyhydroxybenzoic acid, substances having a urethane structure such as urea urethanes, and substances having a polyether structure such as poly(phenylsulfone) ethers. The image stabilizer may be used singly or in combination of two or more.

(Fillers and Other Additives)

The thermal recording material of the present invention may further comprise fillers in the heat-sensitive color forming layer. Examples of the filler include inorganic fillers such as silica, calcium carbonate, kaolin, baked kaolin, diatomaceous earth, clay, talc, titanium oxide, aluminum hydroxide, zinc oxide, zinc hydroxide, barium sulfate and silica treated on the surface; and organic fillers such as polystyrene microballs, Nylon powder, urea-formaline resin fillers, particles of silicone resins, cellulose powder, particles of styrene/methacrylic acid copolymers, particles of vinylidene chloride-based resins, particles of styrene/acrylate copolymers and spherical hollow fine particles of plastics.

The thermal recording material of the present invention may further comprise other additives in the heat-sensitive color forming layer. Examples of the other additive include lubricants such as stearic acid ester waxes, polyethylene waxes and zinc stearate; ultraviolet light absorbers based on benzophenone such as 2-hydroxy-4-benzyloxybenzophenone; ultraviolet light absorbers based on triazol such as benzotriazol, 2-(2'-hydroxy-5'-methylphenyl)benzotriazol, agents providing water resistance such as glyoxazol; dispersants; defoaming agents; antioxidants; and fluorescent dyes.

(Production of Thermal Recording Material)

The process for producing the thermal recording material of the present invention is not particularly limited. The thermal recording material can be produced, for example, by preparing a dispersion (a coating fluid) of the heat-sensitive color forming layer by dispersing the color forming substance, the color forming substance, the sensitizer, the image stabilizer and other additives which are added where necessary in a medium such as an aqueous medium in combination with a suitable binder, followed by coating a support with the coating fluid and drying the formed coating layer. It is preferable that a dispersion comprising the color forming substance, a dispersion comprising the color forming substance and a dispersion comprising the sensitizer are prepared separately, and the dispersion comprising the color forming substance, the color forming substance and the sensitizer is prepared by mixing the obtained dispersions.

Since the color forming substance, the color forming substance and the sensitizer are preferably dispersed as fine particles, it is preferable that a sand mill or a ball mill is used for the preparation of the dispersions.

<Binder>

The binder used in the above is not particularly limited. Examples of the binder include cellulose derivatives such as hydroxyethylcellulose, methylcellulose, methoxycellulose, ethylcellulose and carboxymethylcellulose; polyvinyl alcohols such as polyvinyl alcohol, carboxy-modified polyvinyl alcohol, sulfone-modified polyvinyl alcohol, silicone-modified polyvinyl alcohol and amide-modified polyvinyl alcohol; natural macromolecules such as gelatin, casein, starch and alginic acid; polyacrylic acid; polyacrylic acid esters; polyvinyl acetate; polymethacrylic acid esters; vinyl chloride/vinyl acetate copolymers; ethylene/vinyl acetate copolymers; vinyl acetate/acrylic acid ester copolymers; polyacrylamide; acrylamide/acrylic acid ester copolymers; acrylamide/acrylic acid ester/methacrylic acid terpolymers; isobutylene/maleic anhydride copolymers; styrene/acrylic acid ester copolymers; styrene/butadiene copolymers; styrene/butadiene/acrylate-based copolymers; styrene/maleic anhydride copolymers; methyl vinyl ether/maleic anhydride copolymers; carboxy-modified polyethylene; polyvinyl alcohol/acrylamide block copolymers; polyvinyl pyrrolidone; melamine-formaldehyde resins, urea-formaldehyde resins; polyurethanes; polyamide resins; petroleum resins; and terpene resins. The binder may be used singly or in combination of two or more.

<Support, Undercoat Layer and Backcoat Layer>

The support used in the thermal recording material of the present invention is not particularly limited. Examples of the support include paper such as neutral paper and acidic paper; synthetic paper; regenerated paper using used paper pulp; films; non-woven fabrics; and fabrics.

In the thermal recording material of the present invention, it is preferable that an undercoat layer or a backcoat layer, which comprises an inorganic filler such as silica, calcium carbonate, kaolin, baked kaolin, diatomaceous earth, clay, talc, titanium oxide, aluminum hydroxide, zinc oxide, zinc hydroxide, barium sulfate and silica treated on the surface or an organic filler such as such as polystyrene microballs, Nylon powder, urea-formaline resin fillers, particles of silicone resins, cellulose powder, particles of styrene/methacrylic acid copolymers, particles of vinylidene chloride-based resins, particles of styrene/acrylate copolymers and spherical hollow fine particles of plastics, is formed on the support. When the undercoat layer or the backcoat layer is formed, the formed layer works as the heat insulation layer, and the sensitivity is increased due to the efficient use of the thermal energy from a thermal head or the like. In particular, the undercoat layer and the backcoat layer comprising spherical hollow fine particles of plastics are advantageously used for efficiently increasing the thermal sensitivity.

The spherical hollow fine particles of plastics are hollow fine particles in the expanded condition comprising a thermoplastic resin as the shell and a gas such as the air at the inside. The average diameter of the particles is about 0.2 to 20 µm. When the average diameter of particles (the outer diameter of particles) is smaller than 0.2 µm, problems such as the difficulty in achieving the desired degree of hollowness arise in the production, and cost of the particles increases. When the average diameter exceeds 20 µm, tight contact with the thermal head is suppressed due to decrease in the smoothness of the surface after the coating and the drying, and the effect of increasing the thermal sensitivity is decreased. Therefore, it is preferable that the particles have a diameter in the above range, and the fluctuation of the diameter is small. It is preferable that the spherical hollow fine particles of plastics has a degree of hollowness of 40% or greater and more preferably 90% or greater when the effect of heat insulation is considered. When the degree of hollowness is small, the thermal energy from the thermal head is discharged to the outside of the thermal recording material via the support due to the insufficient effect of heat insulation, and the effect of increasing the thermal sensitivity is poor. The "degree of hollowness" is the ratio of the inner diameter to the outer diameter and expressed as follows:

degree of hollowness=[(inner diameter of hollow fine particle)/(outer diameter of hollow fine particle)]×100

The spherical hollow fine particles of plastics has a thermoplastic resin as the shell as described above. Examples of the thermoplastic resin include polystyrene, polyvinyl chloride, polyvinylidene chloride, polyvinyl acetate, polyacrylic acid esters, polyacrylonitrile, polybutadiene and copolymer resins derived from these resins. Among these resins, copolymer resins comprising vinylidene chloride and acrylonitrile as the main components are preferable.

The binder used for the undercoat layer and the backcoat layer is not particularly limited. Examples of the binder include cellulose derivatives such as hydroxyethylcellulose, methylcellulose, methoxycellulose, ethylcellulose and carboxymethylcellulose; polyvinyl alcohols such as polyvinyl alcohol, carboxy-modified polyvinyl alcohol, sulfone-modified polyvinyl alcohol, silicone modifiedpolyvinyl alcohol and amide-modified polyvinyl alcohol; natural macromolecules such as gelatin, casein, starch and alginic acid; polyacrylic acid; polyacrylic acid esters; polyvinyl acetate; polymethacrylic acid esters; vinyl chloride/vinyl acetate copolymers; ethylene/vinyl acetate copolymers; vinyl acetate/acrylic acid ester copolymers; polyacrylamide; acrylamide/acrylic acid ester copolymers; acrylamide/acrylic acid ester/methacrylic acid terpolymers; isobutylene/maleic anhydride copolymers; styrene/acrylic acid ester copolymers; styrene/butadiene copolymers; styrene/butadiene/acrylate-based copolymers; styrene/maleic anhydride copolymers; methyl vinyl ether/maleic anhydride copolymers; carboxy-modified polyethylene; polyvinyl alcohol/ acrylamide block copolymers; polyvinyl pyrrolidone; melamine-formaldehyde resins, urea-formaldehyde resins; polyurethanes; polyamide resins; petroleum resins; and terpene resins.

In the thermal recording material of the present invention, an overcoat layer may be formed on the color forming layer from a resin soluble in water such as cellulose derivatives and polyvinyl alcohols, an emulsion soluble in water of a styrene-butadiene copolymer or terpene resin, a resin insoluble in water or a material obtained by adding fillers, monomers and oligomers such as isocyanates and unsaturated compounds and crosslinking agents to these materials.

The thermal recording material of the present invention may be a multicolor thermal recording material which comprises a plurality of heat-sensitive color forming layers using various color forming substances having different color tones.

The thermal recording material of the present invention is characterized in that the thermal recording material exhibits excellent storage properties, in particular, excellent oil resistance and resistance to moisture under heat, of image portions and excellent storage properties, in particular, heat resistance, of undeveloped portions and can be advantageously used in the field where the excellent properties for storage of recorded images are required such as labels for food processed by microwave ovens, parking tickets, delivery labels and tickets.

EXAMPLES

The present invention will be described more specifically with reference to examples in the following. However, the present invention is not limited to the examples.

The composition of reaction products in Examples and Comparative Examples was obtained in accordance with the gel permeation chromatography under the following condition.

Chromatograph: manufactured by TOSOH Corporation; HLC-8120GPC
Column: one column having a diameter of 7.8 mm and a length of 30 mm; SHODEX ASAHIPAK GF-310HQ
Temperature of column: 40° C.
Moving phase: dimethylformamide
Flow rate: 0.5 ml/minute
Detector: RI In Examples and Comparative Examples, the properties of the prepared thermal recording materials were evaluated in accordance with the following methods.

(1) Oil Resistance

In the prepared thermal recording material, color was formed using a thermal printing apparatus [manufactured by OKURA ELECTRIC Co., Ltd.] under a printing voltage of 20 V at a pulse width of 3 ms, and the color density of the portion of color formation (the image portion) was measured using a reflection densitometer [manufactured by GRETAGMACBETH Company; "RD-918"]. Then, a drop of cotton seed oil was placed on the image portion. After the resultant sample was left standing at 20° C. under 65% RH for 24 hours, the color density was measured.

(2) Resistance to Moisture Under Heat

In the prepared thermal recording material, color was formed using a thermal printing apparatus [manufactured by OKURA ELECTRIC Co., Ltd.] under a printing voltage of 20 V at a pulse width of 3 ms, and the color density of the portion of color formation (the image portion) was measured using a reflection densitometer [manufactured by GRETAGMAC-BETH Company; "RD-918"]. After the resultant sample was left standing at 60° C. under 80% RH for 24 hours, the color density was measured.

(3) Heat Resistance

In the prepared thermal recording material, the color density of a portion where no color was formed (a portion of no color formation) was measured using a reflection densitometer [manufactured by GRETAGMACBETH Company; "RD-918"]. After the sample was left standing at 80° C. or 100° C. for 24 hours, the color density was measured.

Example 1

Into a reactor, 35 g (0.14 moles) of 4,4'-dihydroxydiphenylsulfone (the purity: 99.8% by mass), 15 g (0.06 moles) of 2.4'-dihydroxydiphenylsulfone (the purity: 96.5% by mass) and 200 g of dimethylformamide were placed, and a solution was prepared. To the prepared solution, 14 g (0.35 moles) of sodium hydroxide was added. The obtained solution was heated at 70° C., and a solution prepared by dissolving 38 g (0.15 moles) of 4,4'-bis(chloromethyl)biphenyl into 120 g of dimethylformamide was added dropwise over 0.5 hours. When the addition was completed, the obtained solution was heated at 110° C., and the reaction was allowed to proceed for 5 hours. When the reaction was completed, the reaction mixture was slowly added into 2,000 g of a 0.1% by mass hydrochloric acid at 30° C. over 0.5 hours, and the resultant mixture was stirred for 2 hours. The formed crystals were separated by filtration and washed with water. The obtained crystals and 500 g of a 20% by mass aqueous solution of methanol were placed into a reactor, heated at 70° C. for 2 hours and then cooled at 25° C. The formed crystals were separated by filtration, washed with water and dried, and 70 g of a reaction product was obtained. The obtained reaction product was analyzed in accordance with the gel permeation chromatography and found to be a compound represented by general formula (1) having the following composition with the values of n:

$n=0$ (the molecular weight: 250); the retention time: 12.9 minutes, the relative peak area: 4.9%
$n=1$ (the molecular weight: 678); the retention time: 12.0 minutes, the relative peak area: 23.2%
$n=2$ (the molecular weight: 1,106); the retention time: 11.2 minutes, the relative peak area: 23.7%
$n=3$ (the molecular weight: 1,534); the retention time: 10.7 minutes, the relative peak area: 19.1%
$n=4$ (the molecular weight: 1,962); the retention time: 10.4 minutes, the relative peak area: 12.7%
$n=5$ (the molecular weight: 2,390); the retention time: 10.0 minutes, the relative peak area: 7.3%
$n=6$ (the molecular weight: 2,818); the retention time: 9.7 minutes, the relative peak area: 3.3%
$n=7$ (the molecular weight: 3,246); the retention time: 9.4 minutes, the relative peak area: 1.2%
$n=8$ (the molecular weight: 3,674); the retention time: 9.2 minutes, the relative peak area: 0.3%
$n=9$ (the molecular weight: 4,102); the retention time: 8.9 minutes, the relative peak area: 0.1%

Example 2

In accordance with the same procedures as those conducted in Example 1 except that sodium hydroxide was used in an amount of 9.2 g (0.23 moles) in place of 14 g (0.35 moles), and 4,4'-bis(chloromethyl) 1,1'-biphenyl was used in an amount of 25.3 g (0.1 mole) in place of 38 g (0.15 moles), 52 g of a reaction product was obtained.

The composition of the obtained reaction product was as follows: n=0: the relative peak area: 8.9%; n=1: the relative peak area: 39.8%; n=2: the relative peak area: 26.8%; n=3: the relative peak area: 12.1%; n=4: the relative peak area: 5.0%; n=5: the relative peak area: 2.1.%; n=6: the relative peak area: 0.5%; n=7: the relative peak area: 0.3%; and n=8: the relative peak area: 0.2%.

Example 3

In accordance with the same procedures as those conducted in Example 1 except that 4,4'-dihydroxydiphenylsulfone (the purity: 99.8% by mass) was used in an amount of 50 g (0.2 moles) in place of 35 g (0.14 moles), and 2,4'-dihydroxydiphenylsulfone was not used, 69 g of a reaction product was obtained. The composition of the obtained reaction product was as follows: n=0: the relative peak area: 4.7%; n=1: the relative peak area: 24.1%; n=2: the relative peak area: 23.1%; n=3: the relative peak area: 18.8%; n=4: the relative peak area: 12.5%; n=5: the relative peak area: 7.2%; n=6: the relative peak area: 3.5%; n=7: the relative peak area: 1.5%; n=8: the relative peak area: 0.4%; and n=9: the relative peak area: 0.2%.

Example 4

In accordance with the same procedures as those conducted in Example 1 except that 2,4'-dihydroxydiphenylsulfone (the purity: 96.5% by mass) was used in an amount of 50 g (0.2 moles) in place of 15 g (0.06 moles), and 4,4'-dihydroxydiphenylsulfone was not used, 65 g of a reaction product was obtained. The composition of the obtained reaction product was as follows: n=0: the relative peak area: 5.0%; n=1: the relative peak area: 23.0%; n=2: the relative peak area: 23.5%; n=3: the relative peak area: 19.0%; n=4: the relative peak area: 13.0%; n=5: the relative peak area: 7.0%; n=6: the relative peak area: 4.0%; n=7: the relative peak area: 1.1%; n=8: the relative peak area: 0.4%; and n=9: the relative peak area: 0.2%.

The results of Examples 1 to 4 are shown in Table 1.

TABLE 1

| | | | Example | | | |
|---|---|---|---|---|---|---|
| | | | 1 | 2 | 3 | 4 |
| Raw material (mole) | | | | | | |
| 4,4'-DHDPS | | | 0.14 | 0.14 | 0.20 | — |
| 2,4'-DHDPS | | | 0.06 | 0.06 | — | 0.20 |
| 4,4'-BCMBP | | | 0.15 | 0.10 | 0.15 | 0.15 |
| Reaction product (g) | | | 70 | 52 | 69 | 65 |
| n | molecular weight | retention time | relative peak area (%) | | | |
| 0 | 250 | 12.9 | 4.9 | 8.9 | 4.7 | 5.0 |
| 1 | 678 | 12.0 | 23.2 | 39.8 | 24.1 | 23.0 |
| 2 | 1106 | 11.2 | 23.7 | 26.8 | 23.1 | 23.5 |
| 3 | 1534 | 10.7 | 19.1 | 12.1 | 18.8 | 19.0 |
| 4 | 1962 | 10.4 | 12.7 | 5.0 | 12.5 | 13.0 |
| 5 | 2390 | 10.0 | 7.3 | 2.1 | 7.2 | 7.0 |
| 6 | 2818 | 9.7 | 3.3 | 0.5 | 3.5 | 4.0 |
| 7 | 3246 | 9.4 | 1.2 | 0.3 | 1.5 | 1.1 |
| 8 | 3674 | 9.2 | 0.3 | 0.2 | 0.4 | 0.4 |
| 9 | 4102 | 8.9 | 0.1 | — | 0.2 | 0.2 |

Notes:
DHDPS: dihydroxydiphenylsulfone
BCMBP: bis(chloromethyl)biphenyl

Example 5

A dispersion of a color forming substance (Fluid A) was prepared by finely pulverizing and dispersing 10 parts by mass of 3-dibutylamino-6-methyl-7-anilinofluorane, 10 parts by mass of a 10% by mass aqueous solution of polyvinyl alcohol and 30 parts by mass of water for 4 hours using a sand mill. Separately, a dispersion of a color forming substance (Fluid B) was prepared by finely pulverizing and dispersing 10 parts by mass of the reaction product obtained in Example 1, 10 parts by mass of a 10% by mass aqueous solution of polyvinyl alcohol and 30 parts by mass of water for 3 hours using a sand mill. A dispersion of silica (Fluid C) was prepared by finely pulverizing and dispersing 10 parts by mass of silica [manufactured by MIZUSAWA INDUSTRIAL CHEMICALS, Ltd.; "MIZUKASIL (a registered trade name): P-527"], 10 parts by mass of a 10% by mass aqueous solution of polyvinyl alcohol and 30 parts by mass of water for 3 hours using a sand mill. A dispersion of zinc stearate (Fluid D) was prepared by finely pulverizing and dispersing 10 parts by mass of zinc stearate, 10 parts by mass of a 10% by mass aqueous solution of polyvinyl alcohol and 30 parts by mass of water for 3 hours using a sand mill. A resin fluid (Fluid E) was prepared by mixing 40 parts by mass of non-expandable plastic hollow fine particles of [the content of solid components: 24% by mass; the average particle diameter: 3 μm; the degree of hollowness: 90%], 10 parts by mass of a styrene/butadiene copolymer latex [manufactured by ZEON Corporation; "NIPOL (a registered trade name) LX430"] and 50 parts by mass of water under stirring using a disperser.

A coating fluid for a color forming layer was prepared by mixing 5 parts by mass of Fluid A, 20 parts by mass of Fluid B, 20 parts by mass of Fluid C and 2.5 parts by mass of Fluid D under stirring using a disperser. A coating fluid for an undercoat layer was prepared by mixing 5 parts by mass of Fluid C and 10 parts by mass of Fluid E under stirring using DISPAX.

A fine quality paper having a unit weight of 60 g/m$^2$ was coated with the coating fluid for an undercoat layer in an amount such that a coating layer having a thickness of 3 g/m$^2$ was formed. The formed coating layer was dried, and a paper having an undercoat was obtained. The undercoat layer formed above was coated with the coating fluid for a color forming layer in an amount such that a color forming layer having a thickness of 5 g/m$^2$ was formed. The formed layer was dried and treated by a calender under a pressure of 0.98 MPa, and a thermal recording material of the present invention was prepared. The prepared thermal recording material was then evaluated.

Example 6

A thermal recording paper was prepared and evaluated in accordance with the same procedures as those conducted in Example 5 except that a dispersion of a color forming substance (Fluid B) was prepared using the reaction product obtained in Example 2 in place of the reaction product obtained in Example 1.

Example 7

A thermal recording paper was prepared and evaluated in accordance with the same procedures as those conducted in Example 5 except that a dispersion of a color forming substance (Fluid B) was prepared using the reaction product obtained in Example 3 in place of the reaction product obtained in Example 1.

Example 8

A thermal recording paper was prepared and evaluated in accordance with the same procedures as those conducted in Example 5 except that a dispersion of a color forming substance (Fluid B) was prepared using the reaction product obtained in Example 4 in place of the reaction product obtained in Example 1.

Example 9

A thermal recording paper was prepared and evaluated in accordance with the same procedures as those conducted in Example 5 except that a dispersion of a color forming substance (Fluid B) was prepared using 7 parts by mass of the reaction product obtained in Example 1 and 3 parts by mass of 4-allyloxy-4'-hydroxydiphenylsulfone in place of 10 parts by mass of the reaction product obtained in Example 1.

Example 10

A thermal recording paper was prepared and evaluated in accordance with the same procedures as those conducted in Example 5 except that a fluid of a color forming substance (Fluid B) was prepared using 7 parts by mass of the reaction product obtained in Example 1 and 3 parts by mass of 4,4'-dihydroxydiphenylsulfone in place of 10 parts by mass of the reaction product obtained in Example 1.

Example 11

A thermal recording paper was prepared and evaluated in accordance with the same procedures as those conducted in Example 5 except that a dispersion of a color forming substance (Fluid B) was prepared using 7 parts by mass of the reaction product obtained in Example 1 and 3 parts by mass of 2,4'-dihydroxydiphenylsulfone in place of 10 parts by mass of the reaction product obtained in Example 1.

Comparative Example 1

A thermal recording paper was prepared and evaluated in accordance with the same procedures as those conducted in Example 5 except that a dispersion of a color forming substance (Fluid B) was prepared using 4,4'-dihydroxydiphenylsulfone in place of the reaction product obtained in Example 1.

Comparative Example 2

A thermal recording paper was prepared and evaluated in accordance with the same procedures as those conducted in Example 5 except that a dispersion of a color forming substance (Fluid B) was prepared using a polycondensation product of 4,4'-dihydroxydiphenylsulfone and bis(2-chloroethyl) ether (phenolic hydroxyl group at both ends) [manufactured by NIPPON SODA Co., Ltd.; "D-90"] in place of the reaction product obtained in Example 1.

Results of evaluation of the thermal recording materials of Examples 5 to 11 and Comparative Examples 1 to 2 are shown in Table 2.

TABLE 2

| | Color density of image portions | | | Color density of undeveloped portions | | |
|---|---|---|---|---|---|---|
| | before test | oil resistance | resistance to moisture under heat | before test | heat resistance at 80° C. | heat resistance at 100° C. |
| Example 5 | 0.81 | 0.79 | 0.81 | 0.09 | 0.09 | 0.10 |
| Example 6 | 0.85 | 0.80 | 0.85 | 0.09 | 0.09 | 0.13 |
| Example 7 | 0.52 | 0.52 | 0.50 | 0.09 | 0.09 | 0.10 |
| Example 8 | 0.97 | 0.90 | 0.92 | 0.09 | 0.09 | 0.15 |
| Example 9 | 1.12 | 1.02 | 1.05 | 0.09 | 0.11 | 0.19 |
| Example 10 | 1.05 | 1.02 | 0.95 | 0.09 | 0.09 | 0.16 |
| Example 11 | 1.09 | 1.04 | 0.98 | 0.09 | 0.09 | 0.18 |
| Comparative Example 1 | 0.95 | 0.50 | 0.70 | 0.10 | 0.11 | 0.17 |
| Comparative Example 2 | 0.95 | 0.89 | 0.85 | 0.09 | 0.11 | 0.29 |

As clearly shown in Table 2, the thermal recording materials of Examples 5 to 11 using the compounds of the present invention as the color forming substance exhibited more excellent oil resistance and resistance to moisture under heat of image portions and heat resistance of undeveloped portions than those of thermal recording materials using the compounds of Comparative Examples 1 and 2 as the color forming substance.

INDUSTRIAL APPLICABILITY

The diphenylsufone bridged compound of the present invention is a novel substance and useful as the color forming substance of thermal recording materials. The thermal recording material of the present invention using the diphenylsulfone bridged compound of the present invention as the color forming substance exhibits excellent oil resistance and resistance to moisture under heat of image portions and heat resistance of undeveloped portions and can be advantageously used in the field where the excellent properties for storage of recorded images are required such as labels for food processed by microwave ovens, parking tickets, delivery labels and tickets

The invention claimed is:

1. A diphenylsulfone bridged compound represented by general formula (1):

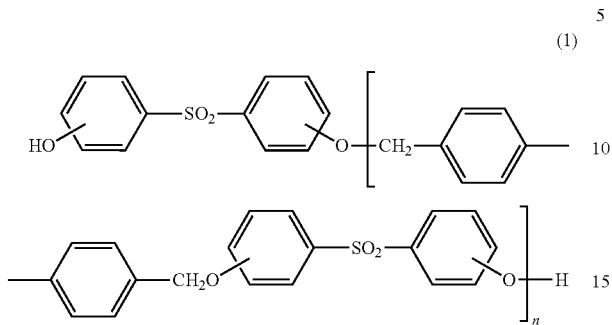
(1)

wherein n represents an integer of 1 to 10.

2. A color forming substance for thermal recording comprising a diphenylsulfone bridged compound represented by general formula (1):

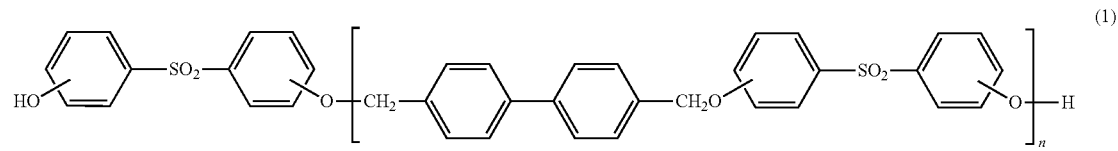
(1)

wherein n represents an integer of 1 to 10.

3. A thermal recording material comprising a heat-sensitive color forming layer which comprises a color forming substance for thermal recording comprising a diphenylsulfone bridged compound represented by general formula (1):

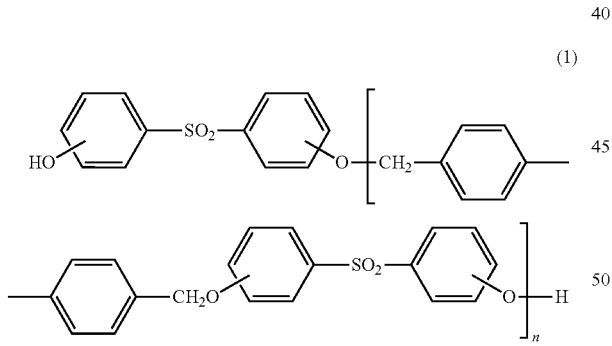
(1)

wherein n represents an integer of 1 to 10, and a color forming substance comprising a colorless or light-colored leuco dye, and is disposed on a support.

* * * * *